US012635854B2

(12) United States Patent (10) Patent No.: US 12,635,854 B2
Lee et al. (45) Date of Patent: May 26, 2026

(54) MOTOR-DRIVEN ENDOSCOPE

(71) Applicant: MEDINTECH INC., Seoul (KR)

(72) Inventors: Chi Won Lee, Namyangju-si (KR);
Myung Joon Kim, Gwacheon-si (KR)

(73) Assignee: MEDINTECH INC., Seoul (KR)

( * ) Notice: Subject to any disclaimer, the term of this
patent is extended or adjusted under 35
U.S.C. 154(b) by 355 days.

(21) Appl. No.: 18/026,826

(22) PCT Filed: Nov. 25, 2020

(86) PCT No.: PCT/KR2020/016772
§ 371 (c)(1),
(2) Date: Mar. 17, 2023

(87) PCT Pub. No.: WO2022/059848
PCT Pub. Date: Mar. 24, 2022

(65) Prior Publication Data
US 2023/0329530 A1 Oct. 19, 2023

(30) Foreign Application Priority Data
Sep. 18, 2020 (KR) ........................ 10-2020-0120377

(51) Int. Cl.
A61B 1/00 (2006.01)
A61B 1/005 (2006.01)

(52) U.S. Cl.
CPC ...... A61B 1/00131 (2013.01); A61B 1/00128
(2013.01); A61B 1/0057 (2013.01); A61B
1/0016 (2013.01)

(58) Field of Classification Search
CPC ... A61B 1/0016; A61B 1/0057; A61B 1/0052;
A61B 1/00121; A61B 1/00128
See application file for complete search history.

(56) References Cited

U.S. PATENT DOCUMENTS

2008/0119695 A1* 5/2008 Ueno ................... A61B 1/0016
600/152
2010/0191053 A1 7/2010 Grarcia et al.
(Continued)

FOREIGN PATENT DOCUMENTS

CN 103517664 A 1/2014
JP 2002-051972 A 2/2002
(Continued)

OTHER PUBLICATIONS

International Search Report for PCT/KR2020/016772 mailed Jun.
11, 2021 from Korean Intellectual Property Office.
(Continued)

*Primary Examiner* — Alexandra L Newton
(74) *Attorney, Agent, or Firm* — Harvest IP Law, LLP

(57) ABSTRACT

A motor-driven endoscope includes: an insertion unit which
is configured so that at least a part from one side thereof, and
which includes a curve unit that is configured to be bent
when being pulled by a wire inserted therein; a grip unit
which is provided at one side of the insertion unit and is held
by a user to input a driving input; a plurality of motors for
transferring driving power so as to steer the curve unit; and
a tension adjustment unit which is provided at the other side
of the insertion unit and receives a rotating force from the
motors to pull each wire, wherein the tension adjustment
unit and the motor are configured to be coupled to or
uncoupled from each other, and the tension adjustment unit
is configured to receive the rotating force from the motor
when coupled to the motor.

13 Claims, 16 Drawing Sheets

(56) References Cited

U.S. PATENT DOCUMENTS

| | | |
|---|---|---|
| 2011/0263983 A1 | 10/2011 | Peszynski |
| 2011/0295063 A1 | 12/2011 | Umemoto et al. |
| 2015/0080658 A1 | 3/2015 | Chung et al. |
| 2019/0069968 A1 | 3/2019 | Sholev |
| 2019/0125458 A1 | 5/2019 | Shelton, IV et al. |
| 2020/0275984 A1 | 9/2020 | Brisson et al. |
| 2022/0040450 A1* | 2/2022 | Haubert ................. A61B 34/71 |

FOREIGN PATENT DOCUMENTS

| | | |
|---|---|---|
| KR | 10-0881811 B1 | 2/2009 |
| KR | 10-2015-0030949 A | 3/2015 |
| KR | 10-2015-0056241 A | 5/2015 |
| WO | 2011-108161 A1 | 9/2011 |
| WO | 2019-136345 A1 | 7/2019 |
| WO | 2022-060565 A1 | 3/2022 |
| WO | 02/065933 A1 | 8/2022 |

OTHER PUBLICATIONS

The extended European Search Report of European Patent Application No. 20954424.2 dated Aug. 9, 2024.
Office Action of Chinese Patent Application No. 202080105313.7 dated Dec. 31, 2024.

* cited by examiner

MOTOR-DRIVEN ENDOSCOPE

CROSS REFERENCE TO PRIOR APPLICATIONS

This application is the 35 U.S.C. 371 national stage of International application PCT/KR2020/016772 filed on Nov. 25, 2020; which claims priority to Korean Patent Application No. 10-2020-0120377 filed on Sep. 18, 2020. The entire contents of each of the above-identified applications are hereby incorporated by reference.

TECHNICAL FIELD

The present disclosure relates to a motor-driven (or motorized) endoscope and, more particularly, to a motor-driven endoscope that may be automatically directed (or steered) in response to user inputs.

BACKGROUND ART

An endoscope is designed to enter a body cavity, obtain images of a lesion, and if necessary, to treat the lesion while an operator is viewing the images thereof. The diameter of the endoscope is gradually decreasing as the size of image sensors has recently been reduced. The function of the endoscope is being improved so that the endoscope may be more accurately operated.

Such endoscopes may be categorized as a rigid endoscope and a flexible endoscope depending on the characteristics of an insertion part that may be inserted into the body cavity. Among such endoscopes, a flexible endoscope is configured such that a bending portion may be provided on the insertion part. That is, the bending portion may be bent in response to manipulation of a user so that the tip of the insertion part may be deformed to a variety of angles. As a simple configuration for bending, a wire is disposed along the insertion part. When the wire is pulled in response to the manipulation of the user, a change of direction may be performed toward one side.

However, as the above endoscope, a manual endoscope in which a user pulls a wire connected to a dial by turning the dial is still widely used. An example of such a manual endoscope is disclosed in Korean Patent No. 0881811.

DISCLOSURE

Technical Problem

The present disclosure proposes a motor-driven endoscope that may overcome limitations of manual endoscopes of the related art and may be directed (or steered) by a simple manipulation.

Technical Solution

In order to achieve the above objective, provided is a motor-driven endoscope including: an insertion part configured such that at least a portion thereof from one side is insertable into a body cavity and including a bending portion configured to bend in response to wires inserted in the insertion portion being pulled; a gripping part provided on one side of the insertion part and having a configuration allowing a user to input driving inputs by holding the gripping part; a plurality of motors transmitting power to steer the bending portion; and a tension adjustment part provided on the other side of the insertion part and configured to pull the wires by receiving rotational force from the motors. The tension adjustment part and the motors may be configured to be coupled to and decoupled from each other. The tension adjustment part may be configured to receive the rotational force from the motors when coupled to the motors.

The tension adjustment part may be connected to each of the plurality of wires for steering the bending portion in top and bottom directions and left and right directions, and may be configured to independently adjust tension of each of the plurality of wires.

The plurality of wires may be four wires, and the tension adjustment part may include four tension adjustment modules. Each of the tension adjustment modules may include: a wire holder configured to fix a tip portion of a corresponding one of the wires; and a power transmission unit configured to rotate by receiving power from a corresponding one of the motors so as to allow the wire holder to linearly move.

In addition, the plurality of motors may be fixed to an external device.

The power transmission unit may include: a screw configured to rotate by receiving power from the corresponding one of the motors; a nut provided on one side of the wire holder and matching the screw; and a wire holder guide guiding the wire holder so that the wire holder is movable in a longitudinal direction of the screw.

The tension adjustment part may further include limiters configured to adjust distances of stroke of the wire holders, respectively.

Each of the wire holders may be configured to fix and release the corresponding one of the wires depending on user selection.

The motor-driven endoscope may further include a connector body having one side connected to the other side of the insertion part and the other side connected to an image processing device or a light source device. The tension adjustment part may be provided inside the connector body.

The connector body may include: an extension connector configured to be fixed to an extension extending from the gripping part; and a connector frame configured such that the tension adjustment part is fixed to the connector frame.

The extension connector may have a connection hole configured to communicate with a hollow space inside the insertion part when the extension is connected to the extension connector.

The connector body may include at least four first pulleys provided between the connection hole and the four wire holders and configured to rotate while supporting the four wires, respectively.

Each of the plurality of wires may be connected at one end to the bending portion, extends through the gripping part, and may be connected at the other end to a corresponding one of the wire holders.

The gripping part may include a plurality of second pulleys configured to rotate following movement of the wires while supporting the wires, respectively.

The gripping part may be gun-shaped and may include a bent portion so as to be held by a user. The second pulleys may be provided inside the bent portion.

The gripping part may be implemented as a keypad or a joystick for adjustment in top and bottom directions and left and right directions.

The motor-driven endoscope may further include a control part configured to control operation of the plurality of motors in response to an input generated using the input part. The control part may cooperatively perform motor control for adjusting the bending portion upward and motor control for adjusting the bending portion downward and may cooperatively perform motor control for adjusting the bending portion to the left and motor control for adjusting the bending portion to the right.

When bending the bending portion upward, the control part may control operation of a pair of motors of the plurality of motors to pull a top wire for upward adjustment of the plurality of wires and to push a bottom wire for downward adjustment of the plurality of wires.

When bending the bending portion to the left, the control part may control operation of a pair of motors of the plurality of motors to pull a left wire for leftward adjustment of the plurality of wires and to push a right wire for rightward adjustment of the plurality of wires.

When bending the bending portion to the left, the control part may control operation of a pair of motors of the plurality of motors to pull a top wire for leftward adjustment of the plurality of wires and to push a right wire for rightward adjustment of the plurality of wires.

The control part may be provided on the image processing device or the light source device.

Advantageous Effects

The motor-driven endoscope according to the present disclosure may be automatically manipulated in response to simple inputs generated by a user so as to maximize the convenience of the user and reduce the time required for the user to become skilled in manipulation of the endoscope.

BEST MODE

Figure 1:
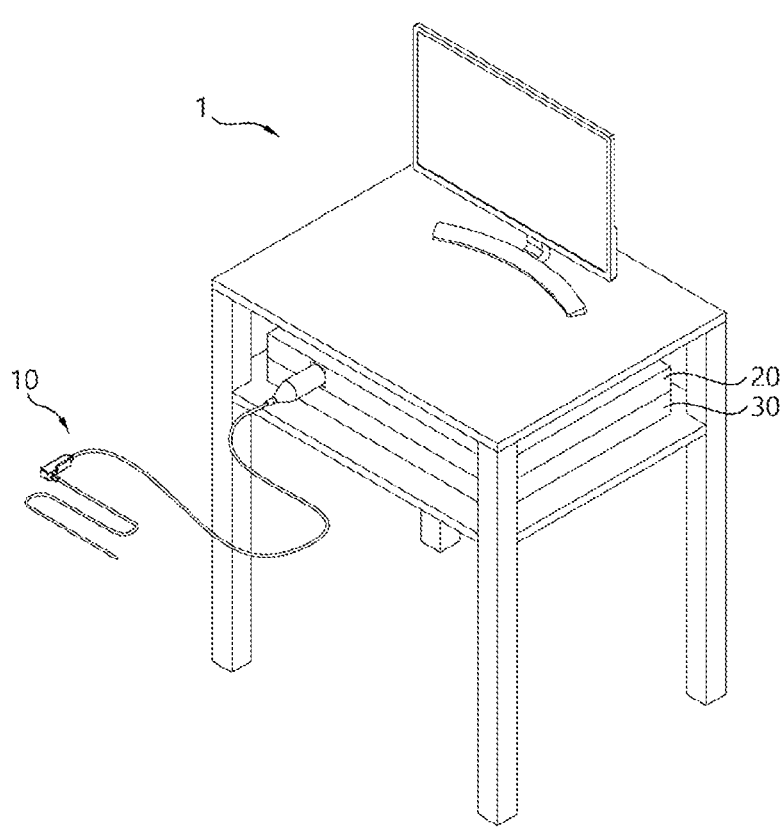
FIG. 1 is a conceptual view illustrating a system including a motor-driven endoscope according to the present disclosure.

Hereinafter, a motor-driven endoscope according to embodiments of the present disclosure will be described in detail with reference to the accompanying drawings. In the following description of embodiments, the names of respective components may be referred to using different names in the field of the art to which the present disclosure pertains. However, when there is functional similarity or sameness, such components may be regarded as being equivalent even in the case in which modified embodiments are employed. In addition, signs or symbols added to components are provided for the convenience of description. However, it will be understood that the components to which the signs or symbols are added are not limited by such illustrations in the drawings. Likewise, even in the case in which an embodiment in which some components in the drawings are modified is employed, the embodiment may be regarded as an equivalent configuration when there is functional similarity or sameness. In addition, when a component is regarded as being a component that must be essentially included in light of the technical level of those having ordinary knowledge in the art, a description thereof will be omitted.

FIG. 1 is a conceptual view illustrating a system including a motor-driven endoscope 10 according to the present disclosure.

As illustrated in the figure, the motor-driven endoscope 10 according to the present disclosure may be configured to be inserted into a body cavity and include a gripping part 500 configured such that a user may hold the gripping part 500 to perform operation inputs.

The motor-driven endoscope 10 according to the present disclosure may be a part of an endoscope system. The endoscope system is configured to obtain images from the lesion area. The endoscope system may have a configuration allowing a user to perform a treatment or a procedure while watching images by inserting a tool as required.

The endoscope system may include an image processing device 20 processing an obtained image, a light source device 30 able to selectively emit various types of light as required, and a display part displaying the obtained image. In addition, the endoscope system may additionally include other devices for cleaning and suction.

The motor-driven endoscope 10 according to the present disclosure is configured such that one side thereof may serve as an insertion part 100 to be inserted into the body cavity and the other side thereof is connected to an external device. As an example, when the endoscope system includes the image processing device 20 and the light source device 30, the motor-driven endoscope may be configured to be connected to at least one of the image processing device 20 and the light source device 30 so as to receive power therefrom. In addition, the motor-driven endoscope 10 is configured to be detachably attached to, for example, at least one of the image processing device 20 and the light source device 30. When the motor-driven endoscope 10 is washed after being used, the motor-driven endoscope 10 may be separated from at least one of the image processing device 20 and the light source device 30 so as to be washed.

Hereinafter, the motor-driven endoscope 10 according to the present disclosure will be described in detail with reference to FIGS. 2 to 14C.

Figure 2:
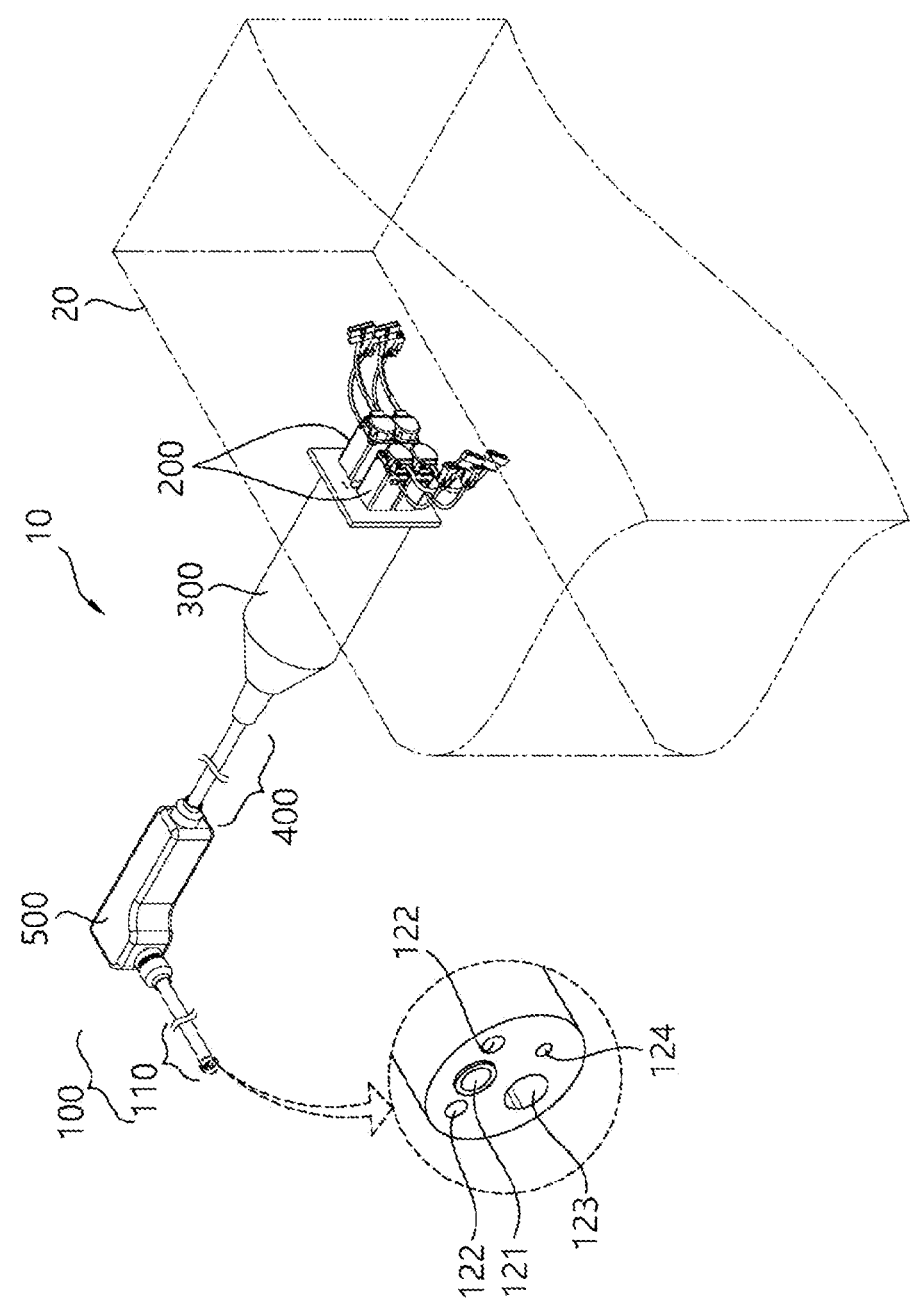
FIG. 2 is a perspective view illustrating the motor-driven endoscope according to the present disclosure.

FIG. 2 is a perspective view illustrating the motor-driven endoscope 10 according to the present disclosure.

As illustrated in the figure, the motor-driven endoscope 10 according to the present disclosure may include the insertion part 100, the gripping part 500, a connector body 300, and motors 200.

The insertion part 100 may be configured to extend in the longitudinal direction and flexibly bend. The insertion part 100 may also be configured such that a tip portion of the insertion part 100 is bent as intended by a user in response to operation of a tension adjustment part 330.

A main working channel 123, a sub-working channel 124, an image sensor 121, and lighting parts 122 may be provided on the tip of the insertion part 100. The main working channel 123 is configured such that a tool for treatment and cure may be inserted thereinto so as to be exposed from the tip. The main working channel 123 may be provided inside the insertion part 100 in the longitudinal direction of the insertion part 100. The sub-working channel 124 is configured such that the diameter thereof is smaller than the diameter of the main working channel 123. The sub-working channel 124 may be configured such that fluid flows therethrough. Since the insertion part 100 having such configurations is widely used, a further detailed description thereof will be omitted.

The gripping part 500 may be configured such that a user may perform an input operation by gripping the gripping part 500. The gripping part 500 may include an input part 600 allowing the user to perform input operations, such as a directing (or directing) input, image capturing, and cleaning water injection, to manipulate the endoscope. The gripping part 500 may be ergonomically designed. In an embodiment, the gripping part 500 may be configured as a gun-shaped part that may be held with fingers without the thumb. When the gripping part 500 is configured to be a gun-shaped part, the input part 600 may be provided on a rear side such that a directing input may be performed with the thumb.

In addition, a plurality of pulleys may be provided inside the gripping part 500. Wires 1000 to be described later extend through the pulleys, respectively, and the pulleys allow the wires 1000 to smoothly move when the tension adjustment part 330 pulls the wires 1000. The internal configuration of the gripping part 500 will be described in detail later with reference to FIG. 10.

An external port communicating with the working channels of the insertion part 100 may be provided on the gripping part 500 or an extension 400 adjacent to the gripping part 500. Since this configuration may be modified variously, a description thereof will be omitted.

The extension 400 is provided on a rear end portion of the gripping part 500 to extend a predetermined length. A connector may be provided on the tip of the extension 400 to be fixed to at least one of the image processing device 20 and the light source device 30. The connector may include a contact terminal through which electrical/optical signals may be transferred when the connector is connected to at least one of the image processing device 20 and the light source device 30. The connector may include the tension adjustment part 330 for receiving power.

The tension adjustment part 330 may include a power transmission unit or a power transmission mechanism that transmits power from the motors 200 to the tension adjustment part 330 and converting rotation to linear movement. The tension adjustment part 330 is configured to generate tension by pulling the wires 1000 in response to the linear movement, thereby finally bending a bending portion 110 of the insertion part 100. The tension adjustment part 330 may be configured to independently adjust tension acting on the plurality of wires 1000 so as to bend the bending portion 110. In an example, when the bending portion is configured to be bendable in four directions, i.e., in the top and bottom directions and the left and right directions, the tension adjustment part 330 may adjust the tension of each of four wires for performing directing in the top and bottom directions and the left and right directions.

In addition, the motor-driven endoscope 10 may include the wires 1000 along the insertion part 100. Each of the plurality of wires 1000 may be disposed in the longitudinal direction of the insertion part 100 and extend through the gripping part 500, with one end thereof being fixed to the tip portion of the above-described insertion part 100, and the other end thereof being fixed to the tension adjustment part 330. As one side of each wire 1000 is pulled by the tension adjustment part 330, the amount and direction of bending of the bending portion 110 may be determined. When the bending portion 110 are configured to be directed (or steered) in the four directions as described above, the wires 1000 may be four wires 1000 enabling the directing in the top and bottom directions and the left and right directions.

The motors 200 may be configured to rotate by receiving electric power. One side of each of the motors 200 may be mechanically connected to the tension adjustment part 330 to transmit power. The number of the plurality of motors 200 may depend on the direction to be directed. In an example, when the wires 1000 are four wires 1000 and the tension adjustment part 330 is configured to adjust the tension of each of the four wires 1000, the motors 200 may also be four motors 200.

In addition, as described above, the motors 200 may be configured to be detachably attached to the tension adjustment part 330, and may be fixed to at least one of the image processing device 20 and the light source device 30.

In addition, although not shown in the drawings, a control part controlling the amount of rotation of motors 200 on the basis of signals generated by the input part 600 manipulated by the user may be provided. The control part may also be provided on at least one of the image processing device 20 and the light source device 30.

Hereinafter, the tension adjustment part 330 and the motors 200 will be described in detail with reference to FIGS. 3 to 9.

Figure 3:
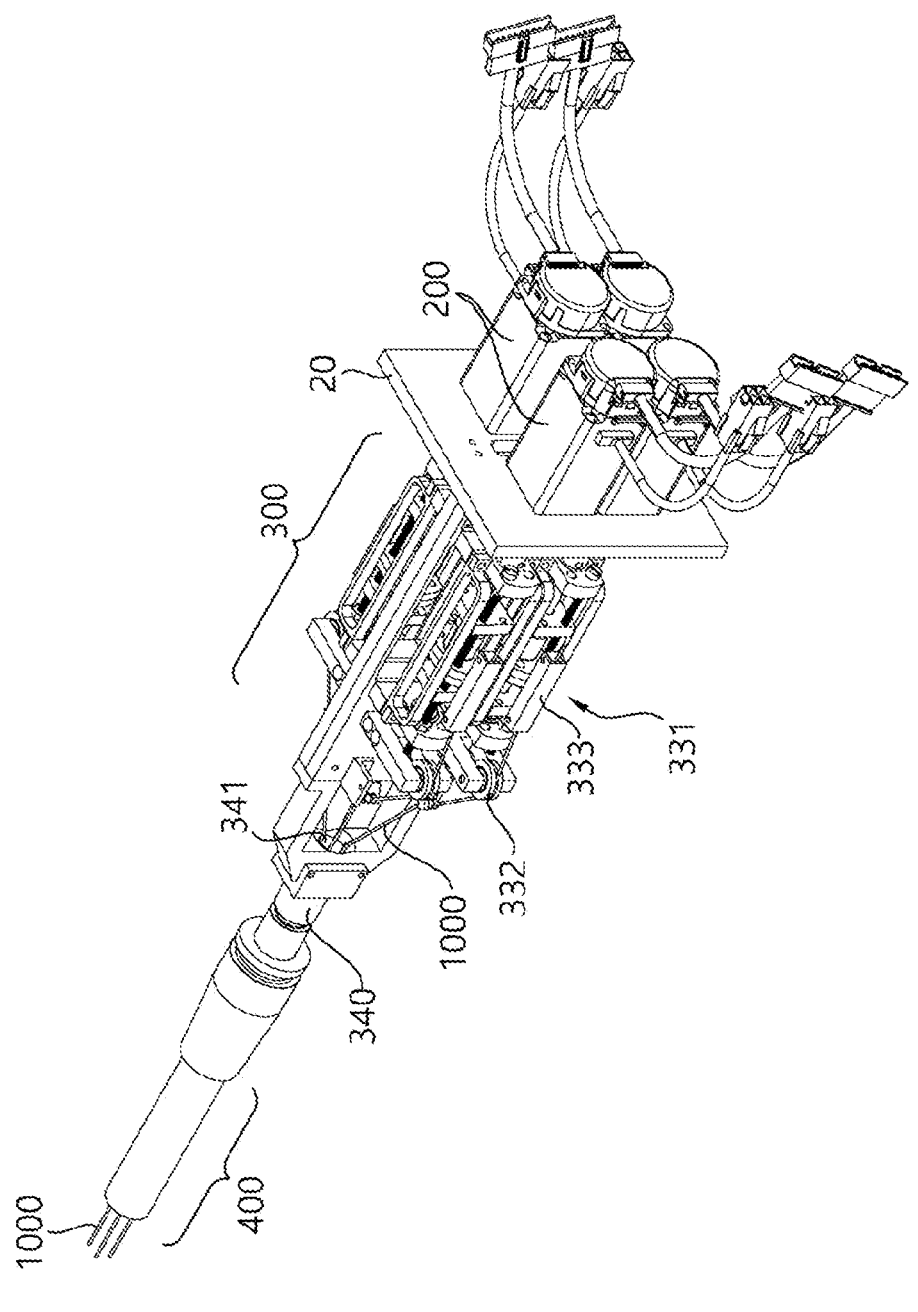
FIG. 3 is a perspective view illustrating a configuration of the motors and the connector body.
Figure 4:
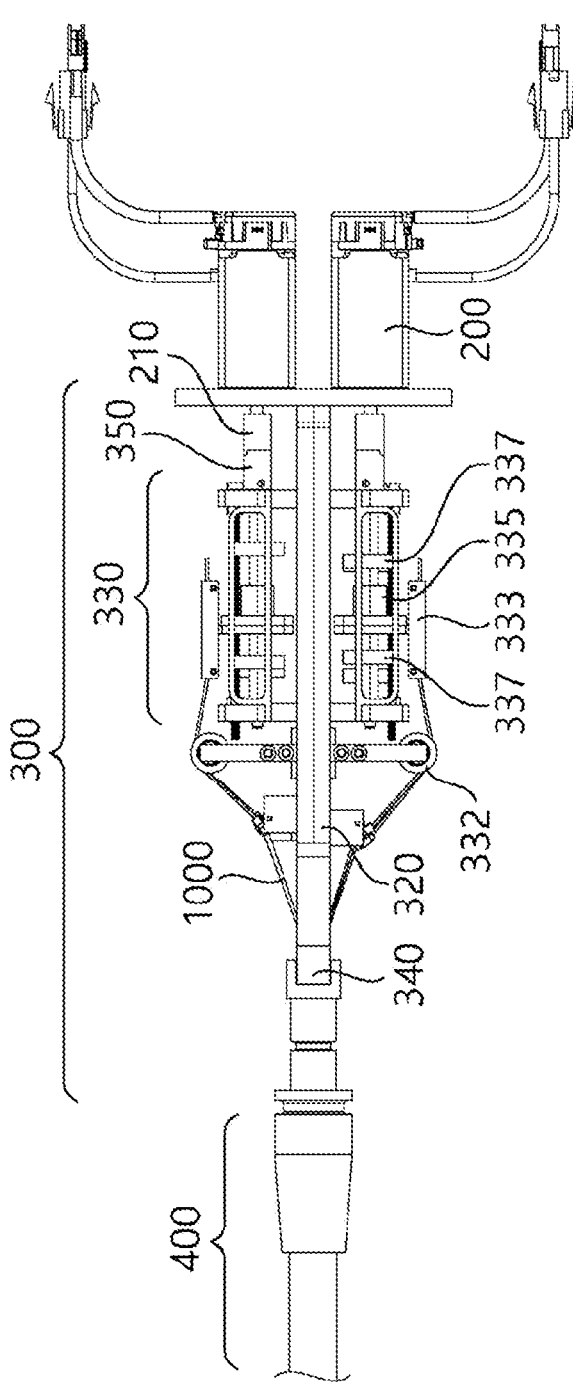
FIG. 4 is a plan view illustrating the configuration of FIG. 3.

FIG. 3 is a perspective view illustrating a configuration of the motors 200 and the connector body 300, and FIG. 4 is a plan view illustrating the configuration of FIG. 3.

Referring to FIGS. 3 and 4, the motors 200 may be fixed to at least one of the image processing device 20 and the light source device 30 to transmit power toward the front, i.e., toward the tension adjustment part 330. For the convenience of description, the description of a connector housing 310 forming the outer portion of the connector body 300 is omitted.

The four motors 200 may be independently controlled to adjust the amount of bending in each of the four directions. The four motors 200 may be disposed in a 2×2 arrangement for space efficiency.

The rotors of the motors 200 are provided adjacent to the connector body 300. The connector body 300 may be connected to the rotors in the axial direction (hereinafter, referred to as the longitudinal direction) of the rotors to receive power.

Components including a connector frame 320, the tension adjustment part 330, first pulleys 332, an extension connector 340 may be provided inside the connector body 300.

The connector frame 320 provides a base to which components of the connector may be fixed. When one side of the connector frame 320 is fixed to the extension 400 and the other side of the connector frame 320 is fixed to at least one of the image processing device 20 and the light source device 30, the position of the connector frame 320 may be reliably fixed. Although the connector frame 320 having the shape of a plate is illustrated in FIGS. 3 and 4, this is only an example and the connector frame 320 may be modified to a variety of shapes.

The tension adjustment part 330 may be provided at the rear of the connector frame 320, i.e., to be adjacent to the motors 200. The tension adjustment part 330 may include tension adjustment modules 331. The tension adjustment modules 331 may be four tension adjustment modules 331 receiving power from the above-described motors 200, respectively, and may be provided on the connector frame 320 in a 2×2 arrangement corresponding to the arrangement of the motors 200.

The first pulleys 332 may be disposed between the tension adjustment part 330 and a connection hole 341 to be described later to support the wires 1000. The first pulleys 332 may be configured to support a single wire 1000 at a plurality of points. A plurality of first pulleys 332 may be provided to support respective wires 1000. In addition, the first pulleys 332 may be additionally arranged in the longitudinal direction to minimize friction and facilitate smooth movement when the wires 1000 move linearly.

The extension connector 340 may be configured to be connected and fixed to one side of the extension 400. The extension connector 340 may be provided in front of the connector frame 320, i.e., on one end opposite the portion connected to the motors 200. The extension connector 340 may have the connection hole 341 formed in the central portion and in the forward direction. The connection hole 341 may be configured such that all of the four wires 1000 may be disposed inside the connection hole 341. A boundary of the connection hole 341 adjacent to the tension adjustment part 330 may be cut smoothly to minimize damage to the wires 1000 when the wires 1000 linearly move while in contact with the hole 341. In addition, an extension hole may be configured to support the wires 1000 such that the wires 1000 are not separately fixed, thereby allowing the wires 1000 to freely move in the longitudinal direction depending on tension adjusted by the tension adjustment part 330.

Figure 5:
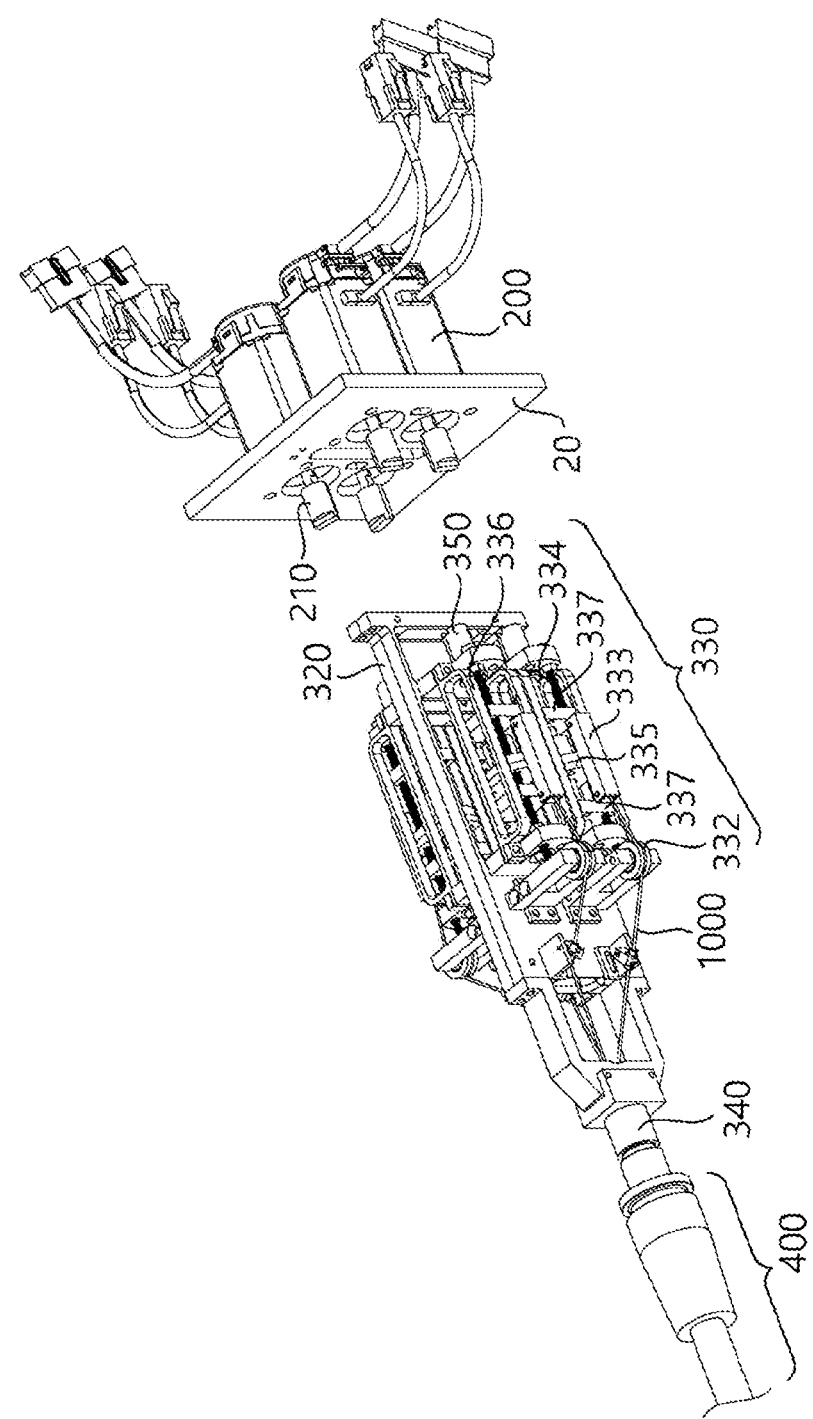
FIG. 5 is a perspective view illustrating the connector body and the motors separated from the connector body.

FIG. 5 is a perspective view illustrating the connector body 300 and the motors 200 separated from the connector body 300.

Referring to FIG. 5, the connector body 300 may be mounted to while being adjacent to and in close contact with at least one of the image processing device 20 and the light source device 30 although the mounting state is not shown. When the connector body 300 is mounted, first connecting portions 210 provided adjacent to the motors 200 and second connecting portions 350 provided adjacent to the tension adjustment part 330 may be in close contact with each other. The first connecting portions 210 and the second connecting portions 350 may be configured such that rotational force may be transmitted when the first connecting portions 210 and the second connecting portions 350 are in close contact. In an example, a male and female structure comprised of protrusions and recesses may be provided. Thus, even in the case that the user does not perform work to connect a separate power transmission path, when the connector body 300 is mounted, all power transmission paths may be connected. However, since the mounting structure may be provided on the connector housing 310 and the connector frame 320 and have a variety of configurations, a further description thereof will be omitted.

Hereinafter, the power transmission unit will be described in detail.

Figure 6:
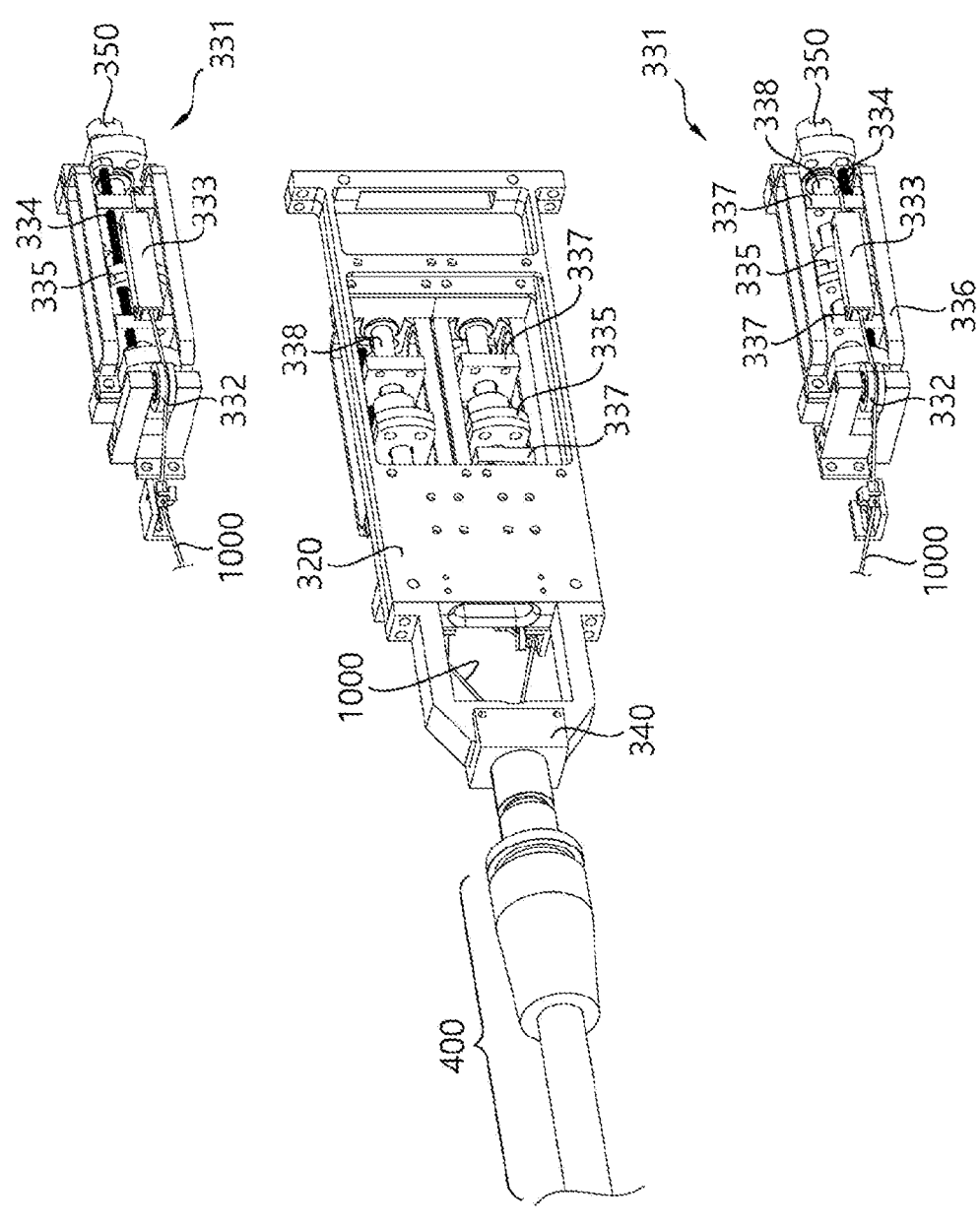
FIG. 6 is a perspective view illustrating the tension adjustment modules separated from the remaining portions of the tension adjustment part.
Figure 7:
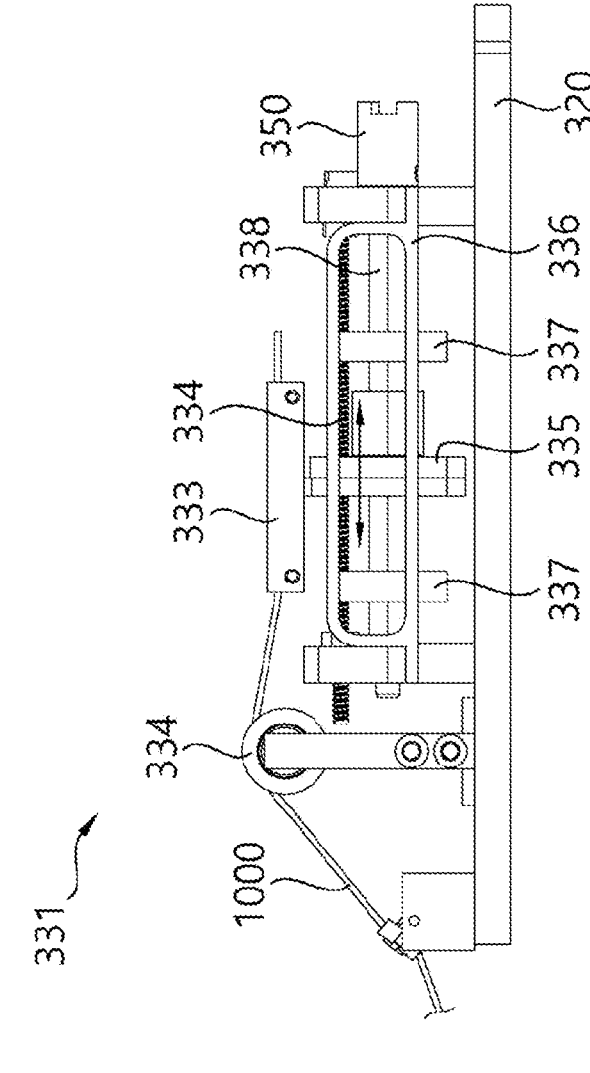
FIG. 7 is a view illustrating an operation state of the tension adjustment part.

FIG. 6 is a perspective view illustrating the tension adjustment modules 331 separated from the remaining portions of the tension adjustment part 330, and FIG. 7 is a view illustrating an operation state of the tension adjustment modules 331.

Referring to FIG. 6, a state in which two tension adjustment modules 331 and two first pulleys 332 are separated from the remaining portions of the tension adjustment part 330 is illustrated. The tension adjustment modules 331 are configured to be elongated in the longitudinal direction. The tension adjustment modules 331 are configured such that the position of a fixing portion 333 may vary as the rotational force is transmitted. Finally, the tension adjustment modules 331 are configured to adjust the tension of the wires 1000. The tension adjustment modules 331 may be connected to the top wire 1100, the bottom wire 1200, the left wire, and the right wire, respectively, to adjust the direction of the bending portion 110. The tension adjustment part 330 is independently configured to independently adjust the tension of each of the wires 1000 connected thereto.

Referring to FIG. 7, each of the tension adjustment modules 331 may include a wire holder 333, a wire holder guide 336, a limiter 337, a limiter position adjustment part 334, a nut 335, and a tension adjustment screw 338.

The wire holder 333 is configured such that the tension of the corresponding wire 1000 is adjusted as the wire holder 333 moves, with one end of the wire 1000 being fixed. In addition, the wire holder 333 may be configured such that the fixing position of the wire 1000 may be adjusted when the wire 1000 is loose as the motor-driven endoscope 10 is used. In this case, the wire holder 333 may be provided to be offset outside in order to improve user accessibility. However, the fixing position of the wire holder 333 is only an example, and the wire holder 333 may be provided inside the tension adjustment part 330.

The wire holder guide 336 may include a guide recess such that the wire holder 333 may move in the longitudinal direction. The nut 335 to be described later may move following rotation of the tension adjustment screw 338, and the wire holder 333 may linearly move depending on the direction of support of the wire holder guide 336 connected to the nut 335.

The limiter 337 is configured to determine the stroke, i.e., the distance and position of reciprocation of the wire holder 333. A pair of pieces of the limiter 337 are provided on both sides of the wire holder 333, and are configured to mechanically limit the wire holder 333. In addition, the adjustment of stroke of the wire holder 333 is not frequently performed, a configuration allowing the position to be manually adjusted may be provided. Accordingly, even in the case that excessive rotational force is transmitted by the motors 200, the limiter 337 may limit the wire holder 333 so as not to exceed a predetermined range, thereby preventing the wire 1000 and the insertion part 100 from being damaged.

The limiter position adjustment part 334 is configured to adjust the positions of the pieces of the limiter 337. The limiter position adjustment part 334 is configured to simultaneously move the pair of pieces of the limiter 337 spaced apart a predetermined stroke distance from each other when the limiter position adjustment part 334 is rotated. The limiter position adjustment part 334 may be a screw-shaped part. As the limiter position adjustment part 334 is rotated, the pair of pieces of the limiter 337 may be moved the same distance in the same direction.

When the wire 1000 has been repeatedly used, the overall length of each wire 1000 may increase. When the length has increased, a suitable level of tension may not act to the wire 1000, thereby reducing directing ability. Thus, in order to adjust the position of reciprocation in response to the increased distance, the pair of pieces of the limiter 337 may be moved rearward by rotating the limiter position adjustment part 334. In this case, since the pair of pieces of the limiter 337 are moved by the rotating screw as described above, the distance between the pieces of the limiter 337 may be maintained. The initial position of the nut may be set between the pair of pieces of the moved limiter 337.

The tension adjustment screw 338 may be configured to extend in the longitudinal direction, and may be configured to rotate when the second connecting portion 350 rotates in engagement with the corresponding first connecting portion 210. One side of the tension adjustment screw 338 may be mechanically connected to one end of the second connecting portion 350 to receive rotational force through gear engagement.

The nut 335 is configured to linearly move in response to rotation of the tension adjustment screw 338 while being supported by a portion of the tension adjustment screw 338. The above-described wire holder 333 is provided on one side of the nut 335. Thus, the wire holder 333 may move following movement of the nut 335.

The tension adjustment screw 338 extends in the longitudinal direction such that the wire holder 333 may linearly move in a reliable manner. The tension adjustment screw 338 may be provided in parallel to the limiter position adjustment part 334. The tension adjustment screw 338 is configured to be inserted into one side of the wire holder 333 or the nut 335 to guide movement of the wire holder 333 or the nut 335.

Figure 8A:
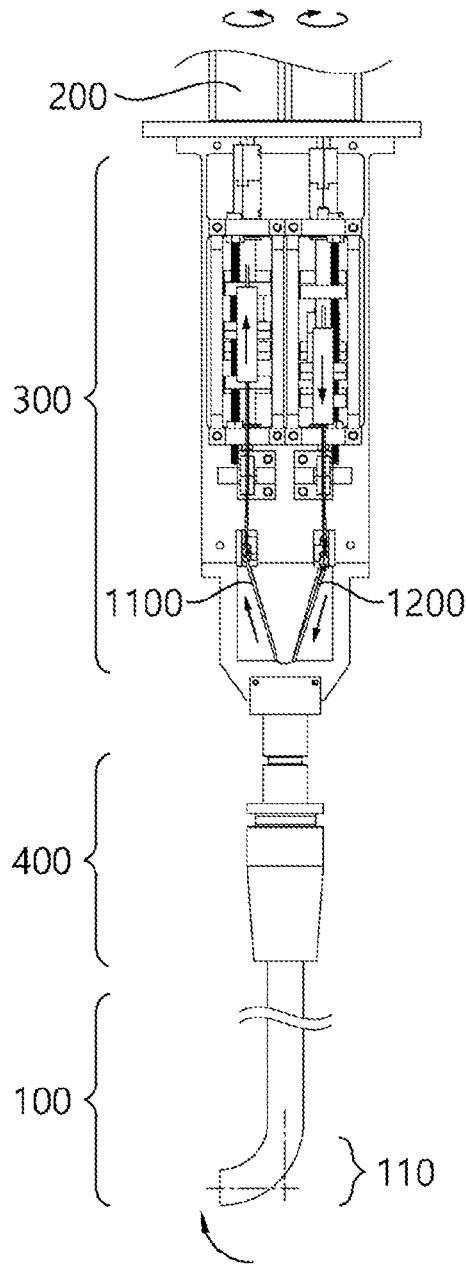
FIGS. 8A and 8B are conceptual views illustrating directing states of the bending portion according to the operation of the tension adjustment part.
Figure 8B:
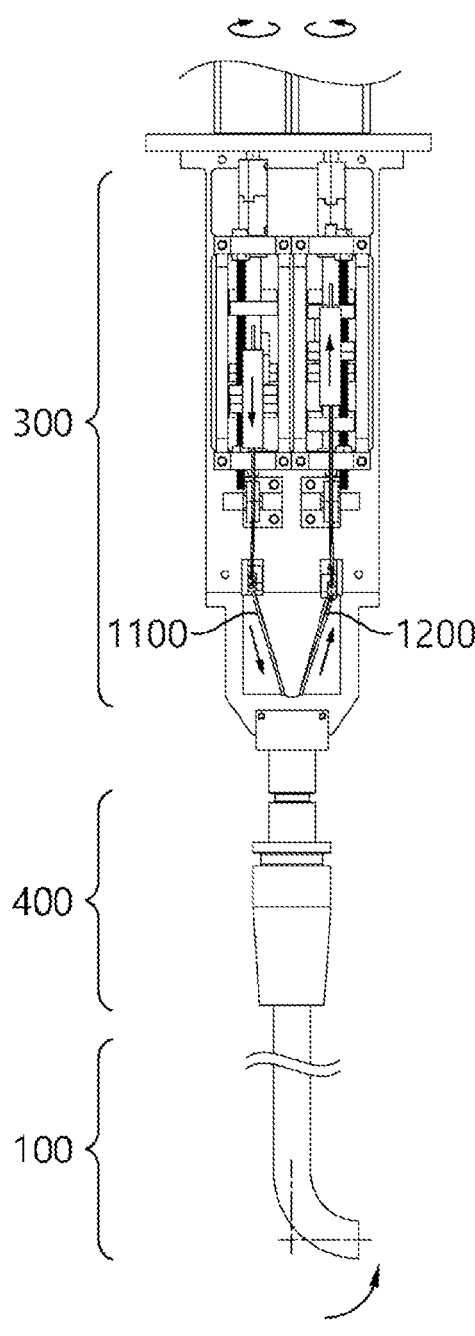

FIGS. 8A and 8B are conceptual views illustrating directing states of the bending portion 110 according to the operation of the tension adjustment part 330.

FIGS. 8A and 8B illustrate a concept of adjusting the tension of each wires 1000 in response to the position of the wire holder 333 being adjusted, thereby bending the bending portion 110 of the insertion part 100. Here, when the tension adjustment part 330 pulls one of the wires 1000, the tension of the wire 1000 provided in the opposite direction may be reduced due to the difference in the radius of curvature of the bending portion 110.

In an example, referring to FIG. 8A, the tension of the bottom wire 1200 is reduced when increasing the tension of the top wire 1100 to bend the bending portion 110 upward. In contrast, referring to FIG. 8B, the tension of the top wire 1100 may be reduced when increasing the bottom wire 1200 to bend the bending portion 110 downward. In this case, the rotation of the motor 200 for adjusting the tension of the top wire 1100 and the rotation of the motor 200 for adjusting the tension of the bottom wire 1200 may be controlled in opposite directions.

Hereinafter, the gripping part 500 will be described in detail with reference to FIGS. 9 to 12B.

Figure 9:
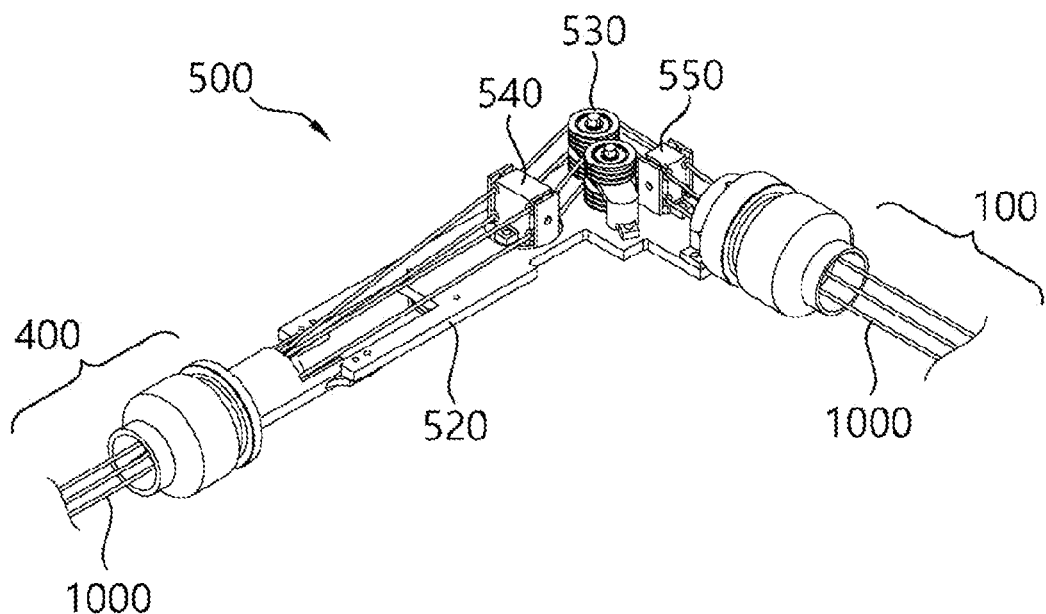
FIG. 9 is a perspective view illustrating the internal structure of the gripping part.
Figure 10:
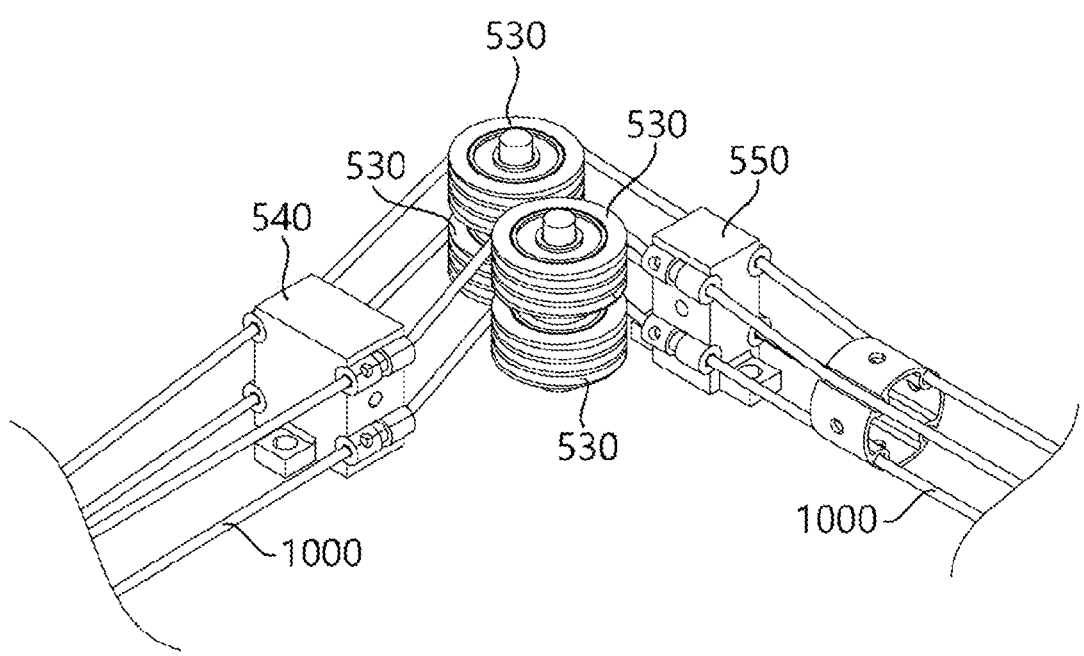
FIG. 10 is a view illustrating the wires extending through the gripping part.

FIG. 9 is a perspective view illustrating the internal structure of the gripping part 500, and FIG. 10 is a view illustrating the wires 1000 extending through the gripping part 500.

Referring to FIG. 9, the gripping part 500 is configuration such that a portion thereof is angled in order to help a user hold the gripping part 500. The insertion part 100 may be connected to the front portion of the gripping part 500, and the extension 400 may be connected to the rear portion of the gripping part 500.

A gripping part frame 520, second pulleys 530, a first wire guide 540, and a second wire guide 550 may be included inside the gripping part 500.

The gripping part frame 520 has a shape corresponding to the shape of the gripping part 500 such that a portion of gripping part frame 520 is bent or angled. The gripping part frame 520 forms a base on which the second pulleys 530, the first wire guide 540, and the second wire guide 550 to be described later may be provided.

However, the above-described configuration of the gripping part 500 is only an example, but there may be a variety of shapes, such as a linear shape and cylindrical shape, which a user may hold.

Referring to FIG. 10, the second pulleys 530 are configured to minimize loss in tension acting on the wire 1000 in the bent portion of the gripping part 500 and to change the direction of movement of the wire 1000. The number of the second pulleys 530 may correspond to the number of the wires 100, and the second pulleys 530 are configured to be rotatable independently. In addition, the second pulleys 530 may be provided at positions inside the gripping part 500 at which the wires 1000 do not interfere with each other.

The first wire guide 540 and the second wire 1000 are configured such that the wire 1000 may maintain a predetermined path at positions upstream and downstream of the second pulleys 530. The first wire guide 540 and the second wire guide 550 cause the wire 1000 to be inserted into holes spaced apart predetermined distances from each other, thereby preventing the wire 1000 from radially moving.

Figure 11:
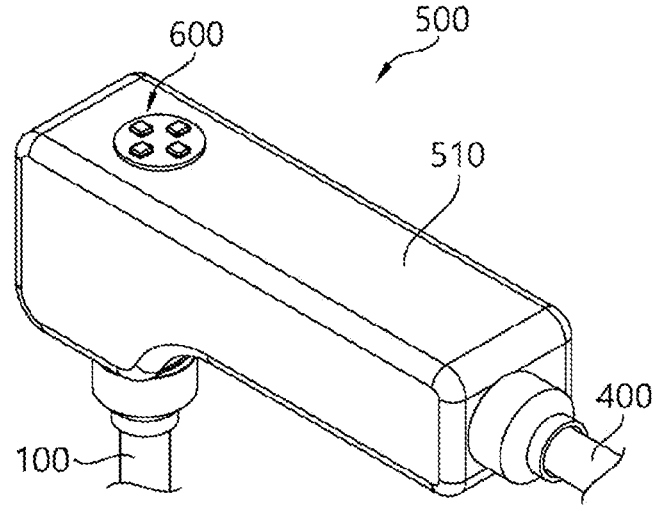
FIG. 11 is a view illustrating the input part of the gripping part.

FIG. 11 is a view illustrating the input part 600 of the gripping part 500.

As illustrated in the figure, the input part 600 may be provided on a portion of the outer surface of a gripping part housing 510 on which the thumb is placed when a user holds the gripping part 500 with a hand. The input part 600 may be configured to generate a directing input by which the bending portion 110 is directed. A four directional directing endoscope, i.e., an endoscope that may be manipulated in the top and bottom directions and the left and right directions, which is widely used, may be configured to perform top-bottom and left-right directional directing inputs. In an example, press buttons for making inputs in respective directions may be provided. Although not shown, the input part 600 may further include function buttons. With the function buttons, inputs for performing special functions required by the user may be generated. For example, the function buttons may allow inputs for additional functions, such as screen capturing, suction, and cleaning, required for use of the endoscope to be received.

Figure 12A:
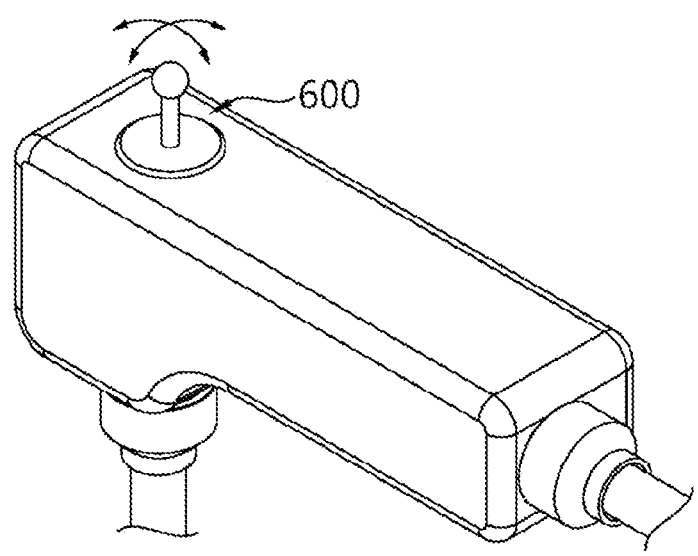
FIGS. 12A and 12B are conceptual views illustrating modified embodiments of the input part.
Figure 12B:
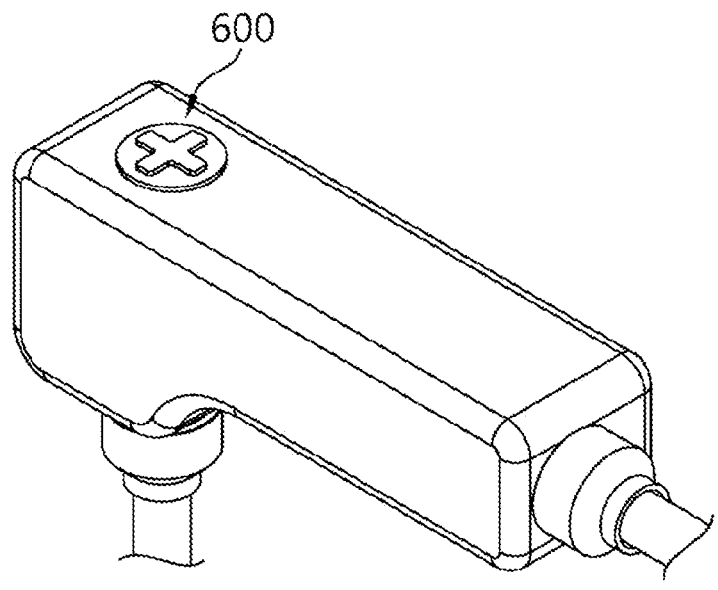

FIGS. 12A and 12B are conceptual views illustrating modified embodiments of the input part 600.

Referring to FIGS. 12A and 12B, the input part 600 may be modified to a variety of shapes. In an example, referring to FIG. 12A, the input part 600 may be implemented as a control stick or a joystick. In addition, referring to FIG. 12B, the input part 600 may be implemented as a disk-shaped button such that a user may generate a manipulation input by pressing the button. However, this is only an example, and the input part 600 may have a variety of configurations that may generate four-directional manipulation inputs, i.e., manipulation inputs in the top and bottom directions and the left and right directions. In addition, the input part may have a variety of configurations able to perform inputs for direction manipulation. For example, the configuration of the input part may be a trackball or the like, with which 360° inputs may be generated, or a diagonal direction light, with which manipulation inputs may be generated on a two-dimensional (2D) plane.

Figure 13A:
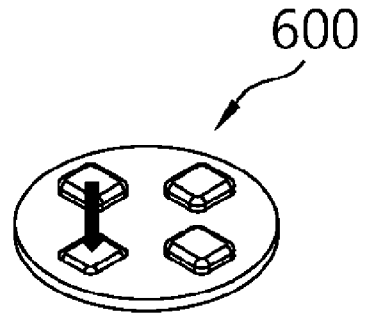
FIGS. 13A, 13B, and 13C are conceptual views illustrating the operation of the tension adjustment part and the directing of the tip of the endoscope in response to an upward manipulation input generated using the input part.
Figure 13B:
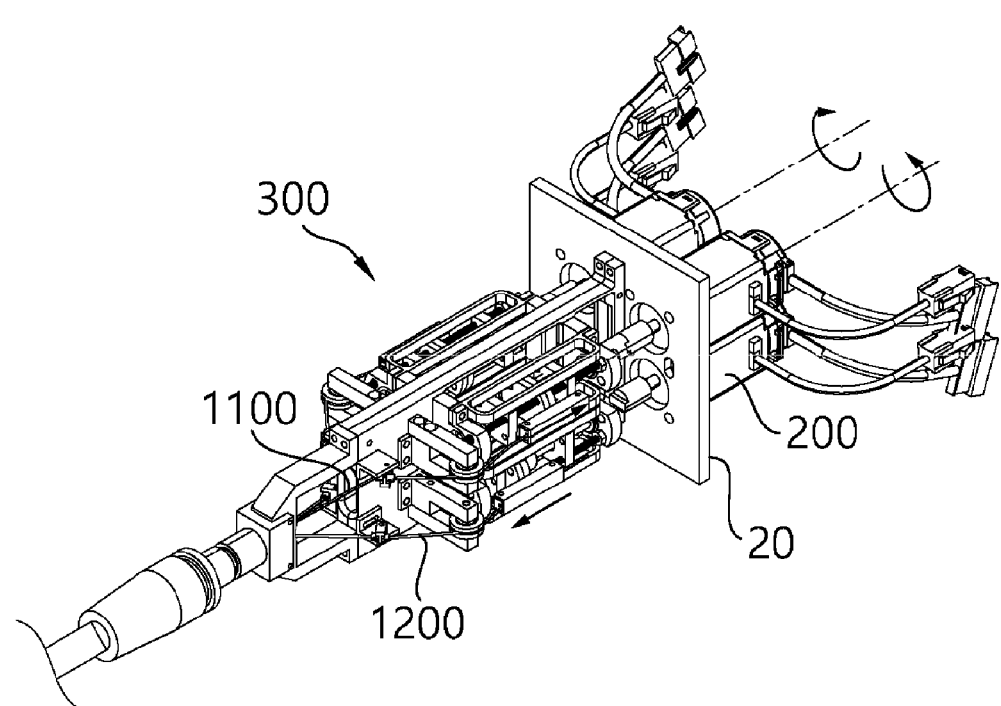
Figure 13C:
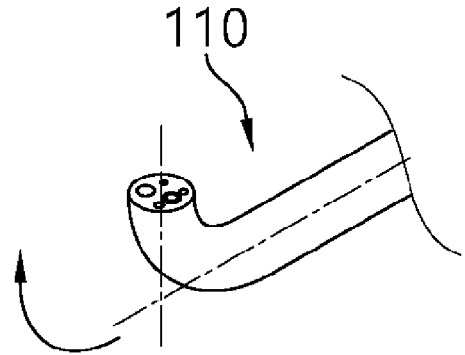

FIGS. 13A, 13B, and 13C are conceptual views illustrating the operation of the tension adjustment part 330 and the directing of the tip of the endoscope in response to an upward manipulation input generated using the input part 600.

Referring to FIG. 13A, first, a user generates an input signal by pressing an upper button of the input part 600. Responsively, the control part may simultaneously control one of the motors 200 to pull the top wire 1100 and another one of the motors 200 to loosen the bottom wire 1200, on the basis of the transmitted input signal. Consequently, as illustrated in FIG. 13B, the wire holder 333 fixed to the top wire 1100 moves backwards, and the wire holder 333 fixed to the bottom wire 1200 moves forwards. As a result, as illustrated in FIG. 13C, the bending portion 110 is finally bent to face upward.

Figure 14A:
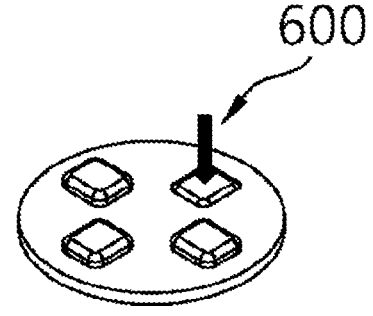
FIGS. 14A, 14B, and 14C are conceptual views illustrating the operation of the tension adjustment part and the directing of the tip of the endoscope in response to a downward manipulation input generated using the input part.
Figure 14B:
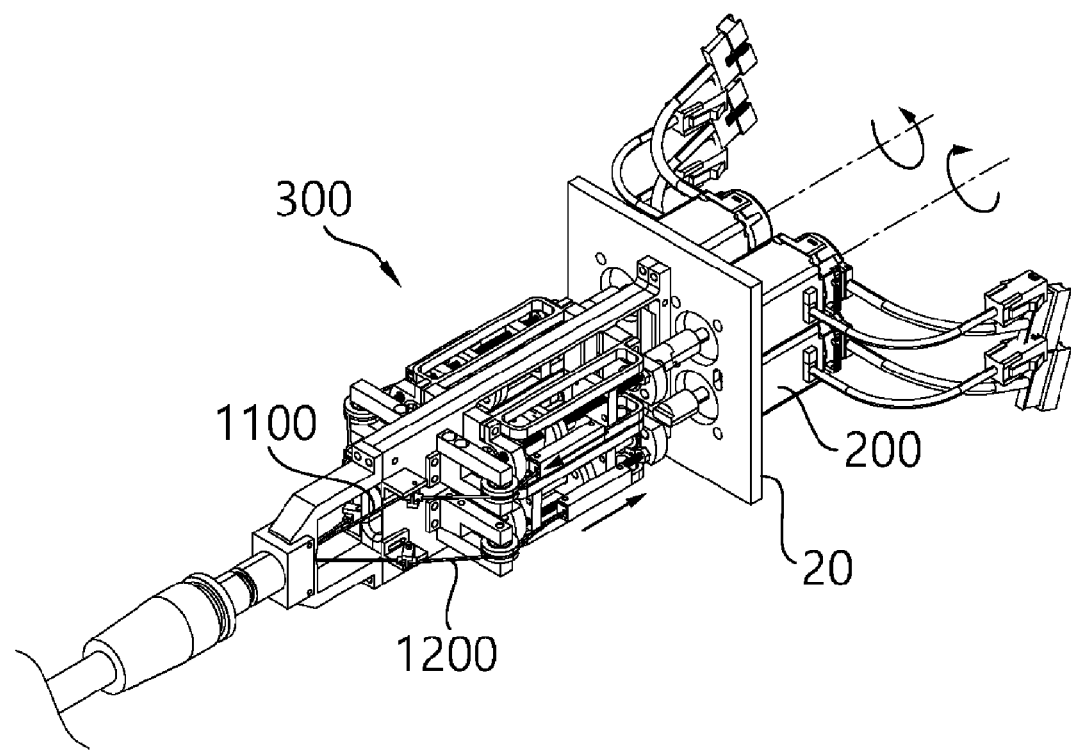
Figure 14C:
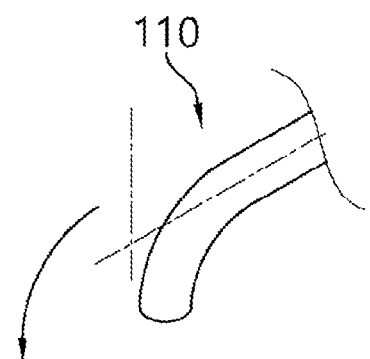

FIGS. 14A, 14B, and 14C are conceptual views illustrating the operation of the tension adjustment part 330 and the directing of the tip of the endoscope in response to a downward manipulation input generated using the input part 600.

Referring to FIG. 14A, when a user presses a lower button of the input part 600, an input signal is generated. Responsively, the control part may simultaneously control one of the motors 200 to pull the bottom wire 1200 and another one of the motors 200 to loosen the top wire 1100, on the basis of the transmitted input signal. Consequently, as illustrated in FIG. 14B, the wire holder 333 fixed to the bottom wire 1200 moves backwards, and the wire holder 333 fixed to the top wire 1100 moves forwards. As a result, as illustrated in FIG. 14C, the bending portion 110 is finally bent to face downward.

Accordingly, the tension adjustment modules 331 may independently adjust the tensions of the wires 1000, and at the same time, the motors 200 may be controlled in a cooperative manner so as to cooperatively adjust the tension of the motors 200 directed in opposite directions.

In addition, although not shown, the directing in the left and right directions may be performed similarly as described with reference to FIGS. 13A to 13C.

As set forth above, the motor-driven endoscope according to the present disclosure may be automatically manipulated in response to simple inputs generated by a user so as to maximize the convenience of the user and reduce the time required for the user to become skilled in manipulation of the endoscope.

The invention claimed is:

1. A motor-driven endoscope comprising:
   an insertion part configured such that at least a portion thereof from one side is insertable into a body cavity and comprising a bending portion configured to bend in response to a plurality of wires inserted in the insertion part being pulled;
   an operation part provided on one side of the insertion part and having a configuration allowing a user to input driving inputs by holding the operation part; and
   a tension adjustment part coupled to the operation part on a side opposite the insertion part and configured to pull the plurality of wires by receiving rotational force from a plurality of motors generating power to steer the bending portion, wherein the operation part includes at least one wire guide inside the gripping part and an input part configured to generate a steering input,
   wherein the at least one wire guide is configured such that the plurality of wires maintain a predetermined path inside the operation part having an angled portion,
   wherein the tension adjustment part is disposed outside the operation part,
   wherein the plurality of wires extend from the tension adjustment part, are inserted into the operation part, pass through the operation part, and extend to the bending portion such that the plurality of wires extend from the tension adjustment part to the bending portion,
   wherein an extending direction of the plurality of wires within the operation part is changed at a position corresponding to the angled portion,
   wherein the at least one wire guide causes the plurality of wires to be inserted into holes spaced apart at predetermined distances from each other,
   wherein the tension adjustment part and the motors are configured to be coupled to and decoupled from each other.

2. The motor-driven endoscope according to claim 1, wherein the tension adjustment part is connected to each of the plurality of wires for steering the bending portion in top and bottom directions and left and right directions.

3. The motor-driven endoscope according to claim 2, wherein
   the tension adjustment part comprises tension adjustment modules,
   each of the tension adjustment modules comprising:
   a wire holder configured to fix a tip portion of a corresponding one of the plurality of wires; and
   a power transmission unit configured to rotate by receiving power from a corresponding one of the motors so as to allow the wire holder to linearly move.

4. The motor-driven endoscope according to claim 3, wherein the plurality of motors are located on a light source device or an image processing device.

5. The motor-driven endoscope according to claim 1, further comprising a connector body having one side connected to an extension extending from the operation part and the other side connected to an image processing device or a light source device, wherein the tension adjustment part is provided inside the connector body.

6. The motor-driven endoscope according to claim 5, wherein the connector body comprises:
   an extension connector configured to be fixed to an extension extending from the operation part; and
   a connector frame configured such that the tension adjustment part is fixed to the connector frame.

7. The motor-driven endoscope according to claim 6, wherein the extension connector has a connection hole configured to communicate, via the extension, with a hollow space inside the insertion part when the extension is connected to the extension connector.

8. The motor-driven endoscope according to claim 2, wherein each of the plurality of wires is connected at one end to the bending portion, extends through the operation part, and is connected at the other end to a corresponding one of the wire holders.

9. The motor-driven endoscope according to claim 8, further comprising a control part configured to control operation of the plurality of motors in response to an input generated using the input part, wherein the control part cooperatively performs motor control for adjusting the bending portion upward and motor control for adjusting the bending portion downward, and the control part cooperatively performs motor control for adjusting the bending portion to the left and motor control for adjusting the bending portion to the right.

10. The motor-driven endoscope according to claim 9, wherein when bending the bending portion upward, the control part controls operation of a pair of motors of the plurality of motors to pull a top wire for upward adjustment of the plurality of wires and to push a bottom wire for downward adjustment of the plurality of wires.

11. The motor-driven endoscope according to claim 9, wherein when bending the bending portion to the left, the control part controls operation of a pair of motors of the plurality of motors to pull a left wire for leftward adjustment of the plurality of wires and to push a right wire for rightward adjustment of the plurality of wires.

12. The motor-driven endoscope according to claim 9, wherein when bending the bending portion to the left, the control part controls operation of a pair of motors of the plurality of motors to pull a top wire for leftward adjustment of the plurality of wires and to push a right wire for rightward adjustment of the plurality of wires.

13. The motor-driven endoscope according to claim 9, wherein the control part is provided on the image processing device or the light source device.

*  *  *  *  *